(12) United States Patent
Hirashima et al.

(10) Patent No.: US 7,935,533 B2
(45) Date of Patent: May 3, 2011

(54) CHROMOSOME MANIPULATION METHOD

(75) Inventors: Kyotaro Hirashima, Chiyoda-ku (JP); Hideki Tohda, Chiyoda-ku (JP); Yuko Hama, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 85 days.

(21) Appl. No.: 12/129,413

(22) Filed: May 29, 2008

(65) Prior Publication Data

US 2008/0311583 A1   Dec. 18, 2008

Related U.S. Application Data

(63) Continuation of application No. PCT/JP2006/323852, filed on Nov. 29, 2006.

(30) Foreign Application Priority Data

Nov. 29, 2005   (JP) ................. 2005-344749

(51) Int. Cl.
*C12N 15/70* (2006.01)
*C12N 15/00* (2006.01)

(52) U.S. Cl. ........................ 435/471; 435/440
(58) Field of Classification Search ........................ None
See application file for complete search history.

(56) References Cited

U.S. PATENT DOCUMENTS

2004/0132192 A1   7/2004   Thoda et al.

FOREIGN PATENT DOCUMENTS

JP   2003-144164   5/2003

OTHER PUBLICATIONS

Tzfira et al.TRENDS in Biotechnology, 2005. vol. 23, No. 12, pp. 567-569.*
Porteus et al (Nature Biotechnology, 2005. vol. 23, No. 8, pp. 967-973).*
Hidekazu Kuwayama, et al., "PCR-mediated Generation of a Gene Disruption Construct Without the use of DNA Ligase and Plasmid Vectors", Nucleic Acids Research, XP002507141, vol. 30, No. 2, Jan. 15, 2002, 5 pages.

Anabelle Decottignies, et al., "*Schizosacharomyces pombe* Essential Genes:A Pilot Study", Genome Research, XP002507139, vol. 13, No. 3, Mar. 2003, pp. 399-406.
Kyotaro Hirashima, et al., "A simple and effective chromosome modification method or large-scale deletion of genome sequences and identification of essential genes in fission yeast" Nucleic Acids Research, vol. 34, No. 2, Jan. 24, 2006, p. 1-7 and a front page.
Kyotaro Hirashima, et al., "Bunretsu Kobo Senshokutai Kaihenho no Koritsuka", Annual Meeting of the Molecular Biology Society of Japan Program Koen Yoshishu, vol. 27, 2004 p. 880 (3PA-346).
Kyotaro Hirashima, et al., "Latour system Senshokutai Kaihen Gijutsu o Oyo shita Aratana Hissu Idenshi Hanteiho", Biotechnology Journal, vol. 6, No. 4, Jul. 1, 2006, pp. 458-461.
Miho Kawahata et al., "Kobo Keishitsu Tenkan ni okeru Sentaku Marker Idenshi no Recycle", The Society for Biotechnology, Japan Taikai Koen Yoshishu, vol. 1996, 1996, p. 313 (1029).
Francoise Längle-Rouault, et al., "A method for performing precise alterations in the yeast genome using recyclable selectable marker", Nucleic Acids Research, vol. 23, No. 15, 1995, pp. 3079-3081.
R. Bruce Wilson, et al., "A recyclable *Candida albicans* URA3 cassette for PCR product-directed gene disruptions", Yeast, vol. 16, No. 1, 2000, pp. 65-70.
Queenie N. Y. Wong, et al., "Efficient and seamless DNA recombineering using a thymidylate synthase A selection system in *Escherichia coli*", Nucleic Acids Research, vol. 33, No. 6, 2005, pp. 1-9.
Kaushik Ghosh, et al., "Cre-loxP biochemistry", Methods 28, 2002, pp. 374-383.
Kirill A. Datsenko, et al., "One-step inactivation of chromosomal genes in *Escherichia coli* K-12 using PCR products", PNAS, vol. 97, No. 12, Jun. 6, 2000, pp. 6640-6645.
György Posfai, et al "Markerless gene replacement in *Escherichia coli* stimulated by a double-strand break in the chromosome", Nucleic Acids Research, vol. 27, No. 22, 1999, pp. 4409-4415.
Christian Grimm, et al., "Genetic engineering of *Schizosaccharomyces pombe*: A system for gene disruption and replacement using the ura4 gene as a selectable marker", Mol Gen Genet, 215, 1988, pp. 81-86.

* cited by examiner

*Primary Examiner* — Celine X Qian
(74) *Attorney, Agent, or Firm* — Oblon, Spivak, McClelland, Maier & Neustadt, L.L.P.

(57) ABSTRACT

A universal method for chromosome modification (deletion of a desired DNA region) which does not require any special enzymes or sequences is provided. Further, a method for determining whether the DNA region to be deleted contains a gene essential for growth of the cell under certain culture conditions is provided by utilizing the chromosome modification method.

12 Claims, 4 Drawing Sheets

SEQUENCE LISTING

<160> NUMBER OF SEQ ID NOS: 20

<210> SEQ ID NO 1
<211> LENGTH: 20

```
<212> TYPE: DNA
<213> ORGANISM: Artificial
<220> FEATURE:
<223> OTHER INFORMATION: synthetic DNA

<400> SEQUENCE: 1
atgtgtgcaa agaaaatcgt                                          20

<210> SEQ ID NO 2
<211> LENGTH: 20
<212> TYPE: DNA
<213> ORGANISM: Artificial
<220> FEATURE:
<223> OTHER INFORMATION: synthetic DNA

<400> SEQUENCE: 2
ttacaaaatt ttttcaagtt                                          20

<210> SEQ ID NO 3
<211> LENGTH: 20
<212> TYPE: DNA
<213> ORGANISM: Artificial
<220> FEATURE:
<223> OTHER INFORMATION: synthetic DNA

<400> SEQUENCE: 3
aaagaggcca accagaagag                                          20

<210> SEQ ID NO 4
<211> LENGTH: 40
<212> TYPE: DNA
<213> ORGANISM: Artificial
<220> FEATURE:
<223> OTHER INFORMATION: synthetic DNA

<400> SEQUENCE: 4
ttattctaca ttaaaccctc aaatttttaa tgtcaaaaaa                    40

<210> SEQ ID NO 5
<211> LENGTH: 40
<212> TYPE: DNA
<213> ORGANISM: Artificial
<220> FEATURE:
<223> OTHER INFORMATION: synthetic DNA

<400> SEQUENCE: 5
tttcgtcaat atcacaagct cgtttactaa cgtagaaagc                    40

<210> SEQ ID NO 6
<211> LENGTH: 20
<212> TYPE: DNA
<213> ORGANISM: Artificial
<220> FEATURE:
<223> OTHER INFORMATION: synthetic DNA

<400> SEQUENCE: 6
gttgttgaag aagttttgtt                                          20

<210> SEQ ID NO 7
<211> LENGTH: 20
<212> TYPE: DNA
<213> ORGANISM: Artificial
<220> FEATURE:
<223> OTHER INFORMATION: synthetic DNA

<400> SEQUENCE: 7
tagggtttaa tgtagaataa                                          20
```

```
<210> SEQ ID NO 8
<211> LENGTH: 40
<212> TYPE: DNA
<213> ORGANISM: Artificial
<220> FEATURE:
<223> OTHER INFORMATION: synthetic DNA

<400> SEQUENCE: 8
gtgggatttg tagctaagct ggatgtcgta aatcaattcc                              40

<210> SEQ ID NO 9
<211> LENGTH: 20
<212> TYPE: DNA
<213> ORGANISM: Artificial
<220> FEATURE:
<223> OTHER INFORMATION: synthetic DNA

<400> SEQUENCE: 9
aagatgacga tgatgatttt                                                    20

<210> SEQ ID NO 10
<211> LENGTH: 20
<212> TYPE: DNA
<213> ORGANISM: Artificial
<220> FEATURE:
<223> OTHER INFORMATION: synthetic DNA

<400> SEQUENCE: 10
gtcgcttctt ctcaacgact                                                    20

<210> SEQ ID NO 11
<211> LENGTH: 20
<212> TYPE: DNA
<213> ORGANISM: Artificial
<220> FEATURE:
<223> OTHER INFORMATION: synthetic DNA

<400> SEQUENCE: 11
atggatgcta gagtatttca                                                    20

<210> SEQ ID NO 12
<211> LENGTH: 21
<212> TYPE: DNA
<213> ORGANISM: Artificial
<220> FEATURE:
<223> OTHER INFORMATION: synthetic DNA

<400> SEQUENCE: 12
ttaatgctga gaaagtcttt g                                                  21

<210> SEQ ID NO 13
<211> LENGTH: 20
<212> TYPE: DNA
<213> ORGANISM: Artificial
<220> FEATURE:
<223> OTHER INFORMATION: synthetic DNA

<400> SEQUENCE: 13
agaattgaga cggcgctgaa                                                    20

<210> SEQ ID NO 14
<211> LENGTH: 40
<212> TYPE: DNA
<213> ORGANISM: Artificial
<220> FEATURE:
<223> OTHER INFORMATION: synthetic DNA
```

```
<400> SEQUENCE: 14
gtccttttgt taaataaaaa ttaggataca ctaggtagat                              40

<210> SEQ ID NO 15
<211> LENGTH: 40
<212> TYPE: DNA
<213> ORGANISM: Artificial
<220> FEATURE:
<223> OTHER INFORMATION: synthetic DNA

<400> SEQUENCE: 15
tttcgtcaat atcacaagct tgttgctttt ttatattaaa                              40

<210> SEQ ID NO 16
<211> LENGTH: 20
<212> TYPE: DNA
<213> ORGANISM: Artificial
<220> FEATURE:
<223> OTHER INFORMATION: synthetic DNA

<400> SEQUENCE: 16
aaacaagact aaagattagt                                                    20

<210> SEQ ID NO 17
<211> LENGTH: 20
<212> TYPE: DNA
<213> ORGANISM: Artificial
<220> FEATURE:
<223> OTHER INFORMATION: synthetic DNA

<400> SEQUENCE: 17
tttttattta acaaaaggac                                                    20

<210> SEQ ID NO 18
<211> LENGTH: 40
<212> TYPE: DNA
<213> ORGANISM: Artificial
<220> FEATURE:
<223> OTHER INFORMATION: synthetic DNA

<400> SEQUENCE: 18
gtgggatttg tagctaagct tttatcgaaa gaaaagaaat                              40

<210> SEQ ID NO 19
<211> LENGTH: 20
<212> TYPE: DNA
<213> ORGANISM: Artificial
<220> FEATURE:
<223> OTHER INFORMATION: synthetic DNA

<400> SEQUENCE: 19
gacagtaaaa gcattaagta                                                    20

<210> SEQ ID NO 20
<211> LENGTH: 20
<212> TYPE: DNA
<213> ORGANISM: Artificial
<220> FEATURE:
<223> OTHER INFORMATION: synthetic DNA

<400> SEQUENCE: 20
gctttaccaa cttcgtcaga                                                    20
```

CHROMOSOME MANIPULATION METHOD

CROSS-REFERENCE TO RELATED APPLICATIONS

The present application is continuation of PCT/JP2006/323852, filed on Nov. 29, 2006, which claims priority to JP 2005-344749, filed on Nov. 25, 2005.

TECHNICAL FIELD

The present invention relates to a chromosome modification technique and provides a method for efficiently removing a specific long region from a chromosome and a method for determining whether the specific region carries a specific gene.

BACKGROUND ART

In this post-genomic era, chromosome engineering is increasing its technological importance. Techniques for development of living organisms with chromosomes carrying desired modifications such as gene disruption, foreign gene insertion and mutagenesis are extremely important in various fields such as molecular biology, basis medicine and agricultural engineering. Various techniques for chromosome modification have been developed to date, including the λ-red recombination system (Non-patent Document 1), the Cre/loxP system (Non-patent Document 2), the Flp/FRT system (Non-patent Document 3) and a system using meganuclease (Non-patent Document 4). These methods have their own characteristics and have drawbacks such as the foreign inserts remaining after chromosome modification, and the difficulty associated with determining the optimal conditions for enzyme expression. Moreover, all these methods not only require specific enzymes and sequences but also are time-consuming and troublesome because two or more steps are generally required to obtain the modified target strain.

Chromosome modification in *S. cerevisae* and *C. albicans* using URA3 (orotidine 5'-phosphate decarboxylase gene) as a selectable marker gene is known (FIG. 1) (Non-patent Documents 5 and 6). FIG. 1 schematically illustrates the URA3 recycling method previously developed in *S. cerevisae* and *C. albicans*. In this method, a modification fragment containing repeated sequences is inserted (FIG. 1). The target DNA region of a chromosome (the parental strain in FIG. 1) is replaced by the DNA fragment carrying a negative selectable marker gene and hence deleted. URA3 as the selectable marker is flanked by repeated sequences (the sequences upstream and downstream of the URA3 selectable marker gene), and the inserted modification fragment enclosed with a dotted line contains the repeated sequences. The URA3 selectable marker gene allows both positive and negative selections. While prototrophs are selected in a uracil-deficient medium, auxotrophs are selected in a medium containing 5-fluoroorotic acid (hereinafter referred to as 5-FOA) in which uracil prototrophs are unable to grow because 5-FOA is an analogue of a uracil precursor and is known to be converted to fluorouracil, a strong growth inhibitor for yeasts (Non-patent Document 7).

Non-patent Document 1: Wong, Q. N. et al. Efficient and seamless DNA recombineering using a thymidylate synthase A selection system in *Escherichia coli*. Nucl. Acids Res. 33, e59 (2005).

Non-patent Document 2: Ghosh, K. & DuyneG. D. Cre-loxP biochemistry. Methods 28, 374-383 (2002).

Non-patent Document 3: Datsenko, K. A. & Wanner, B. L. One-step inactivation of chromosomal genes in *Escherichia coli* K-12 using PCR products. Proc. Natl. Acad. Sci. USA 97, 6640-6645 (2000).

Non-patent Document 4: Posfai, G., Kolisnychenko, V., Bereszki, Z. & Blattner, F. R. Markerless gene replacement in *Escherichia coli* stimulated by a double-strand break in the chromosome. Nucl. Acids Res. 27, 4409-4415 (1999).

Non-patent Document 5: Langle-Rouault, F. & Jacobs, E. A method for performing precise alterations in the yeast genome using are cyclable selectable marker. Nucl. Acids Res. 23, 3079-3081 (1995).

Non-patent Document 6: Wilson, R. B., Davis, D., Enloe, B. M.& Mitchell, A. P. A recyclable *Candida albicans* URA3 cassette for PCR product-directed gene disruptions. Yeast 16, 65-70 (2000).

Non-patent Document 7: Grimm, C., Kohli, J., Murray, J. & Maundrell, K. Genetic engineering of *Schizosaccharomyces pombe*: a system for gene disruption and replacement using the ura4 gene as a selectable marker. Mol. Gen. Genet. 215, 81-86 (1998).

DISCLOSURE OF THE INVENTION

Problems that the Invention is to Solve

The problem that the invention is to solve is to provide a universal method for chromosome modification which does not require any special enzymes or sequences.

Means of Solving the Problems

As a result of their research from the above-mentioned viewpoints, the present inventors have found a way to introduce repeated sequences which allows more efficient chromosome modification using a negative selectable marker gene and have accomplished the present invention. Namely, the present invention provides:

1. A method of deleting a target DNA region from a chromosome in a cell, which comprises:
integrating "a negative selectable marker gene (B)" upstream or downstream of the target DNA region so that the target DNA region and the selectable marker gene are placed between repeated sequences to form "a region (X) comprising the selectable marker gene (B) and the target DNA region" between the repeated sequences, and
then removing the region (X) from the chromosome by homologous recombination and negative selection to obtain cells lacking the region (X).

2. A method of deleting a target DNA region from a chromosome in a cell, which comprises:
integrating a DNA fragment containing "a sequence (A') substantially identical to a specific sequence (A) present downstream of the target DNA region" and "a negative selectable marker gene (B)" connected behind the sequence (A'), upstream of the target DNA region to form "a region (X) comprising the selectable marker gene (B) and the target DNA region" between the substantially identical two sequences [(A) and (A')], and then removing the region (X) from the chromosome by homologous recombination and negative selection to obtain cells lacking the region (X).

3. The method according to 2 mentioned above, wherein the specific sequences (A) and (A') are from 50 bp to 100 bp long.

4. The method according to any one of 1 to 3, wherein the target DNA region is from 500 bp to 500 kbp long.

5. The method according to any one of 1 to 4 mentioned above, wherein the selectable marker gene (B) is an orotidine 5'-phophate decarboxylase gene.

6. The method according to any one of 1 to 5 mentioned above, wherein the target DNA region contains a gene which complements an auxotrophy during cell growth, and homologous recombination and negative selection are carried out under culture conditions under which the gene which complements the auxotrophy is not essential.

7. A method of determining whether a target DNA region deleted from a chromosome in a cell contains a gene essential for growth under desired culture conditions (Z), which comprises:

integrating "a negative selectable marker gene (B)" upstream or downstream of the target DNA region so that the target DNA region and the selectable marker are placed between repeated sequences to form "a region (X) comprising the selectable marker gene (B) and the target DNA region" between the repeated sequences, carrying out homologous recombination and negative selection, wherein the homologous recombination and the negative selection are carried out under the culture conditions (Z), or the homologous recombination and the negative selection are followed by incubation of the resulting cells under the culture conditions (Z), examining cells viable under the culture conditions (Z) for the presence of the target DNA region in the chromosome, and determining that the target DNA region does not contain any genes essential for growth under the culture conditions (Z), if the target DNA region is not present in the chromosome.

8. A method of determining whether a target DNA region deleted from a chromosome in a cell contains a gene essential for growth under desired culture conditions (Z), which comprises:

integrating a DNA fragment comprising "a sequence (A')" substantially identical to a specific sequence (A) present downstream of the target DNA region" and "a negative selectable marker gene (B)" connected behind the sequence (A'), upstream of the target DNA region to form "a region (X) comprising the selectable marker gene (B) and the target DNA region" between the substantially identical two sequences (A) and (A'), carrying out homologous recombination and negative selection, wherein the homologous recombination and the negative selection are carried out under the culture conditions (Z), or the homologous recombination and the negative selection are followed by incubation of the resulting cells under the culture conditions (Z), examining cells viable under the culture conditions (Z) for the presence of the target DNA region in the chromosome, and determining that the target DNA region does not contain any genes essential for growth under the culture conditions (Z), if the target DNA region is not present in the chromosome.

9. The method according to 7 or 8 mentioned above, wherein the target DNA region contains at least two genes.

10. The method according to any one of 7 to 9 mentioned above, wherein the selectable marker gene (B) is an orotidine 5'-phosphate decarboxylase gene.

Effect of the Invention

The chromosome modification according to the present invention is characterized in that no foreign sequences remain after chromosome modification and is universally applicable with efficiency equal to or exceeding that of previous methods. The present invention provides a simple method of confirming whether or not a gene is essential for growth and makes easier deletion of a large DNA area of 100 kb, which has been difficult to delete by previous methods. Further, the chromosome modification according to the present invention can widely be applied, e.g., to bacteria and mammal cells because it utilizes a mechanism common to any organisms, and *Schizosaccharomyces pombe* (hereinafter referred to as *S. pombe*) is a representative model microorganism having a chromosome structure similar to that of higher organisms.

BEST MODE FOR CARRYING OUT THE INVENTION

Figure 1:
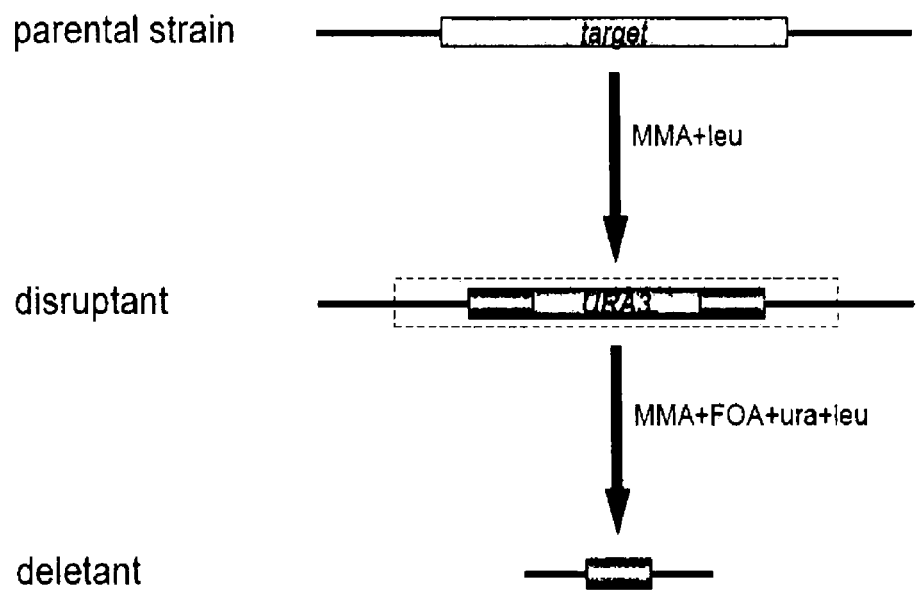
FIG. 1 Schematic representation of the deletion (recycling) of the selectable marker gene using repeated sequences.

The present invention provides a method of deleting a target DNA region from a chromosome in a cell. As the cell, though yeast is used in Examples, a wide variety of cells from bacteria to mammal cells may be used.

For deletion of a target DNA region, firstly, "a negative selectable marker gene (B)" is integrated upstream or downstream of the target DNA region so that the target DNA region and the selectable marker gene (B) are placed between repeated sequences to form "a region comprising the selectable marker gene (B) and the target DNA region" between the repeated sequences. If the chromosome originally has repeated sequences upstream and downstream of the target DNA region, the repeated sequences may be used. But, usually, substantially identical sequences (repeated sequences) are formed upstream and downstream of the target DNA region. For example, a specific sequence (A) originally present downstream of the target DNA region may be used in combination with a substantially identical sequence (A') introduced upstream of the target DNA region so that these two sequences (A) and (A') serve as the repeated sequences. Similarly, a specific sequence originally present upstream of the target DNA region may be used, and further, substantially identical sequences may be introduced both downstream and upstream of the target DNA region to form repeated sequences.

The "negative selectable marker gene (B)" is integrated between the repeated sequences. The selectable marker gene (B) may be integrated upstream or downstream of the target DNA region. The integration of the selectable marker gene (B) and formation of the repeated sequences may be done simultaneously or in an arbitrary order.

Herein, it will be specifically exemplified how to integrate a sequence (A') substantially identical to a specific sequence (A) originally present downstream of the target DNA region together with the selectable marker gene (B), upstream of the target DNA region. Although there are other methods for the integration of the selectable marker gene (B) and the formation of repeated sequences, this method is preferred in view of operational simplicity and efficiency.

The first step in deletion of the target DNA region is integration of a DNA fragment having "a sequence (A') substantially identical to a specific sequence (A) present downstream of the target DNA region" and "the negative selectable marker gene (B)" following the sequence (A'), upstream of the target DNA region, and thereby "a region (X) comprising the selectable marker gene (B) and the target DNA region" is formed between the substantially identical two sequences [(A) and (A')]. Then, upon homologous recombination and negative selection, cells having chromosomes lacking the region (X) are obtained.

In FIGS. 1 to 3 and 5, MMA indicates a MMA minimal medium. The minimal medium used in the Examples described later was also MMA minimal medium. For the composition of MMA minimal medium, see Okazaki et al. (Nucleic Acids Res. 18:6485-6489 (1990)).

Figure 2:
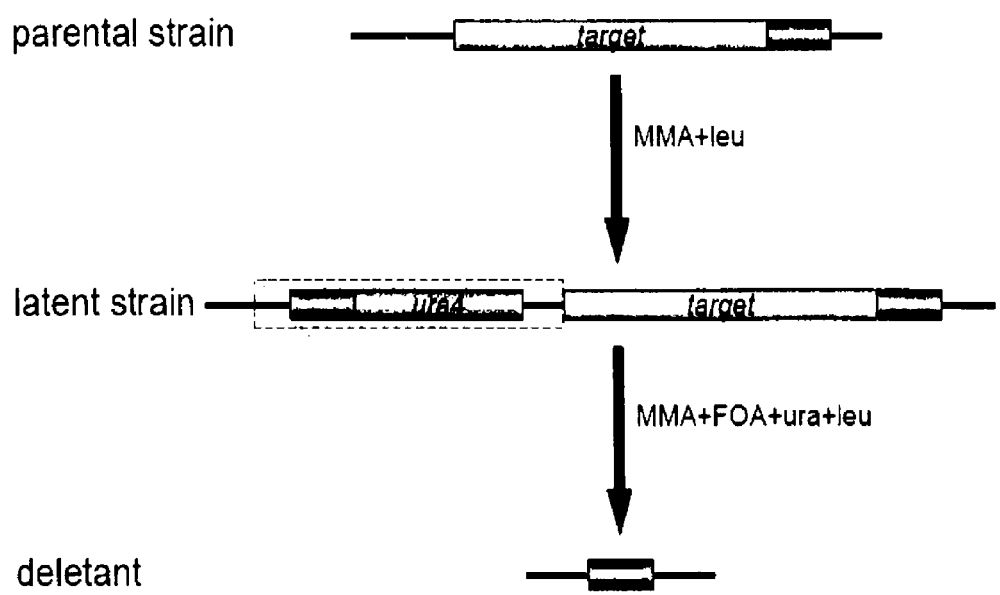
FIG. 2 Schematic representation of the chromosome modification recycling the ura4 gene developed according to the present invention.
Figure 3:
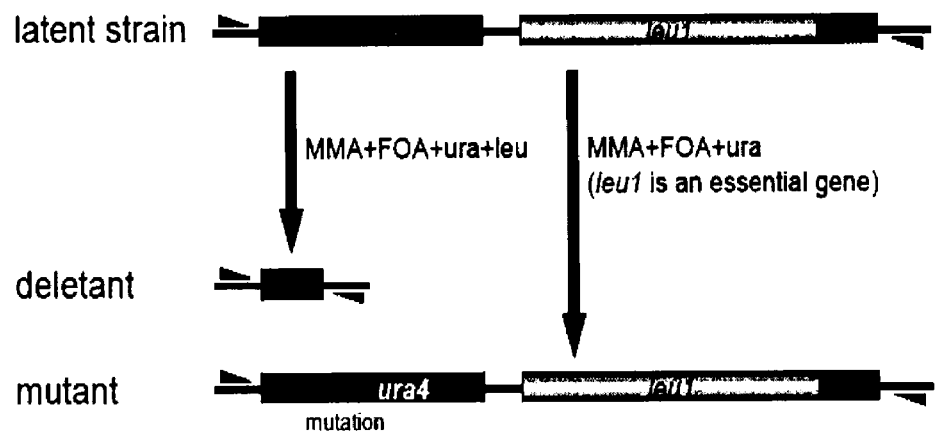
FIG. 3 Schematic representation of chromosome modifications that can occur upon 5-FOA treatment of a latent strain. The closed triangles show the primers used for throughout in FIG. 4.

FIGS. 2 and 3 are schematic representations of chromosome modification recycling the ura4 gene according to the present invention. In the present invention, as shown in the latent strain in FIG. 2, a DNA fragment having a sequence (A') substantially identical to a specific sequence (A) present downstream of the target DNA region (indicated as target in the figure) in the parental strain and a negative selectable marker gene (B) (indicated as ura4 in the figure) connected behind the sequence (A) is introduced upstream of the target DNA region to form "a region (X) comprising the selectable is marker gene (B) and the target DNA region" between the substantially identical sequences [(A) and (A')]. The modification fragment itself does not contain repeated sequences, and it is not until a latent strain is obtained that ura4 is placed between repeated sequences together with the target DNA region. The major difference from previous methods is that the target DNA region to be deleted remains after the modification fragment is introduced. Herein, a cell strain which originally lacks the selectable maker gene "URA" or has a previously inactivated selectable marker gene "URA" should be used. Namely, a uracil auxotroph which requires uracil (ura) in a culture medium is used as the parental stain. A transformant (latent strain) having the selectable marker gene "URA" (indicated as ura4 in the figure) introduced is a uracil prototroph and selected on a uracil-deficient medium.

Then, mutants are selected. Transformants (latent stains) having the selectable marker gene "URA" introduced cannot grow in the presence of 5-FOA (indicated as FOA in the figure), which means that on a medium containing 5-FOA, transformants having the selectable marker gene "URA" introduced cannot grow, while mutants without the selectable marker gene "URA" (or with an inactivated URA gene) (deletants or mutants) are viable (though they require uracil (ura) for growth). Therefore, mutants (deletants or mutants) in which the selectable marker gene "URA" is deleted again (or is inactivated) are selected on a medium containing 5-FOA and (5-fluoroorotic acid) and uracil (FIGS. 2 and 3).

FIG. 3 is a schematic representation of chromosome modification that can occur upon 5-FOA treatment of a latent strain. In FIG. 3, on a medium containing leucine (indicated as leu), strains in which leu1 has been deleted with ura4 by homologous recombination (deletant) are obtained, because the leu1 gene is not essential. On the other hand, on a leucine-deficient medium, strains (mutants) that lack ura4 activity due to mutation but retain leu1 will appear. The leu1 gene compensates the leucine auxotrophy (a selectable marker gene), and in FIG. 3, the target DNA region contains this gene.

In the chromosome modification according to the present invention, though the modification fragment itself does not contain repeated sequences (consists only of the selectable marker gene URA4 and the sequence (A') upstream of the selectable marker gene URA4), the selectable marker gene ura4 and the target DNA region are placed between repeated sequences (the specific sequences A and A') in the latent strain. The one of the major differences from previous methods is that the target DNA region to be deleted remains at the stage of introduction of the modification fragment.

The specific sequence (A) to be used in the present invention may be any sequence present downstream of the target DNA region without any particularly restrictions and is preferably from 50 bp to 1000 bp long, particularly preferably from 200 bp to 400 bp long. Repeated sequences (substantially identical two sequences A and A' flanking the region to be deleted) of such a length would be sufficient to cause homologous recombination. Here, it is meant by substantially identical that they are similar enough to cause homologous recombination. The above-mentioned preferred length applies when a sequence present upstream of the target DNA region is used as the specific sequence, or when specific sequences are introduced both downstream and upstream of the target DNA region to form repeated sequences.

The target DNA region as the target in the present invention is not particularly restricted. The target DNA to be deleted can be from 200 bp to 1000 bp long, and the target DNA region is preferably from 500 bp to 500 kbp, particularly preferably from 1 kbp to 200 kbp. The present invention is characterized in that it enables deletion of a long region, but it is possible to delete a short region close to the above-mentioned minimal length. Further, if desired, an even shorter region below the above-mentioned minimal length, even a singly nucleotide, can be deleted. Deletion of the target DNA region, even if that short, can be confirmed by determining the length between the repeated sequences as described later.

Further, a new sequence may be introduced beyond either repeated sequence at the same time as deletion of the target DNA region according to the present invention, for example, by using a DNA fragment which further has a new arbitrary sequence upstream of the sequence (A') connected in front of the selectable marker gene (B) to construct a chromosome which lacks the target DNA region but has the new arbitrary sequence. The new arbitrary sequence may be, for example, a marker gene.

In the present invention, known negative selectable marker genes may be used as the negative selectable marker gene (B) without any particular restrictions. For example, a "URA" (orotidine 5' phosphate decarboxylase) gene is preferred as the negative selectable marker gene. "URA3" is the "URA" gene of the budding yeast S. cerevisiae, while "URA4" is the "URA" gene of S. pombe. In addition, LYS2·LYS5 relating to lysine synthesis in the budding yeast S. cerevisiae may be used instead of URA3 in combination with α-aminoadipic acid, and the SacB selectable marker gene in *Escherichia coli* may also be used as the negative selectable marker gene.

The homologous recombination in the present invention is a gene targeting method for artificially modifying a specific gene in a genome, and when a DNA fragment having a region homologous to a specific gene in the genome is introduced, recombination occurs at the homologous region to integrate the foreign DNA into the genome.

In the present invention, negative selection is selection in a negative fashion in which selected clones are caused to death. In the present invention, introduction of the selectable marker gene means that cells are caused to death under the specified culture conditions. In cells that survive negative selection, the selectable marker gene has been deleted (with the target DNA region) from the chromosome, or the selectable marker gene in the chromosome has been mutated so as not to function as the selectable marker any longer (while the target DNA region is retained).

These two types of cells obtained by negative selection can be distinguished by amplifying the sequences between the repeated sequences (A) and (A') by PCR or the like and determining the lengths of the amplification products. For example, primers for a sequence downstream of the specific sequence (A) and a sequence upstream of the specific sequence (A') (indicated by triangles in FIGS. 3 and 6) are used to amplify the sequence between the primers, and the lengths of the fragments obtained by the amplification are determined. Cells which give a short fragment (of the length corresponding to the total length of both primers+(A)+(A')) are considered to lack the target DNA region, while cells which give a long fragment (of the length corresponding to the total length of both primers+(A)+(A')+the mutated selective marker gene+the target DNA region) are considered to contain the target DNA region.

When the target DNA region contains a second selectable marker, the two types of cells can be distinguished by the presence or absence of the second selectable marker. For example, when the target DNA region contains a gene which complements an auxotrophy (a second selectable marker), cells which are auxotrophic during cell growth lack the gene which complements the auxotrophy and are judged as cells in which the target DNA has been deleted, while cells which are prototrophic during cell growth retain the gene which complements the auxotrophy and are judged as cells retaining the target DNA.

In the deletion of a target DNA region according to the present invention, the homologous recombination and the negative selection are preferably carried out with a target DNA region containing a gene which complements an auxotrophy during cell growth, under such conditions that a gene which complements the auxotrophy is not essential. In FIG. 3, the target DNA region contains the leu1 (3-isopropylmalate dehydrogenase) gene, and the homologous recombination and the negative selection are carried out by incubation on a medium containing leucine (leu). Namely, incubation is carried out under conditions which secure homologous recombination and negative selection in the absence of the leu1 gene.

The present invention also provides a method of determining whether a target DNA region deleted from a chromosome in a cell contains a gene essential for growth under desired culture conditions (Z).

In the above-mentioned method, a "negative selectable marker gene (B)" is integrated upstream or downstream of the target DNA region so that the target DNA region and the selectable marker are placed between repeated sequence to form a region comprising the selectable marker and the target DNA region between the repeated sequences. This step is carried out in the same manner as in the previously mentioned deletion method of the present invention. It will be specifically exemplified how to integrate the sequence (A') substantially identical to a specific sequence (A) originally present downstream of the target DNA region, together with the selectable marker gene (B), upstream of the target DNA region. Although there are other methods for the integration of the selectable maker gene (B) and the formation of repeated sequences, this method is preferred in view of operational simplicity and efficiency.

The method comprises integrating a DNA fragment comprising "a sequence (A') substantially identical to a specific sequence (A) present downstream of the target DNA region" and "a negative selectable marker gene (B)" connected behind the sequence (A'), upstream of the target DNA region to form "a region (X) comprising the selectable marker gene (B) and the target DNA region" between the substantially identical two sequences (A) and (A'), carrying out homologous recombination and negative selection wherein the homologous recombination and the negative selection are carried out under the culture conditions (Z), or the homologous recombination and the negative selection are followed by incubation of the resulting cells under the culture conditions (Z), examining the cells viable under the culture conditions (Z) for the presence of the target DNA region in the chromosome, and determining that the target DNA region does not contain any genes essential for growth under the culture conditions (Z), if the target DNA region is not present in the chromosome. The respective terms used in the respective steps according to the present invention have the same meanings as in the previously mentioned method for deleting a target DNA region from a chromosome.

In the present invention, "under desired culture conditions (Z)" means that the present invention involves identification of auxotrophs".

FIG. 3. is a schematic representation of the determination method of the present invention. In the latent strain, the leu1 gene as the target DNA region and the ura gene as the selectable marker gene are placed between the specific sequence (A) and the substantially identical sequences (A'), which are located downstream and upstream of them. As shown on the left-hand side of FIG. 3, "under culture conditions (Z)" using a medium containing leu [MMM+5-FOA+ura (uracil)+leu (leucine)], the "leu1" gene is a non-essential gene for growth under the "culture conditions (Z)". Namely, if "deletants" "substantially lacking the target DNA region ("leu1" gene)" grow under the "culture conditions (Z)", the "leu1" gene is judged as non-essential under the culture conditions.

On the other hand, as shown on the right-hand side of FIG. 3, "under culture conditions (Z)" using a leu-deficient medium [MMM+5-FOA+ura], the "leu1" is essential for growth under the "culture conditions (Z)". Namely, if "mutants" "substantially retaining the target DNA region ("leu1" gene)" grow under the culture conditions [in the absence of leu], the "leu1" gene is judged as essential under the culture conditions (Z).

In the present invention, the target DNA region of the previously described length may contain two or more genes, for example, a gene relating to viability such as the "leu1" gene and another gene.

Thus, since the present invention is simple, does not require special operations and does not leave a foreign sequence after deletion of the target DNA sequence from a chromosome, the present invention can be applied repeatedly at other sites. Further, the present invention is simple and does not require introduction of enzymes, which is required by previous methods. Further, while in previous methods, the loxP sequence is separately integrated at two sites in mice for deletion of a very long region, the present invention requires the modification of only one side of the target gene in a chromosome for deletion without modification of the sequence originally present on the other side. Thus, the present invention is much easier and more excellent than previous methods.

The present invention has major features that the target DNA region is retained at the stage of integration of the selectable marker gene, and that the target DNA sequence is deleted extremely efficiently. Using the present invention, it is possible to examine whether or not a gene or chromosome region is essential for growth.

The leu1 gene used in Examples of the present invention is considered as an essential gene in a leucine-deficient medium, but as a non-essential gene in a medium containing leucine. Thus, when the method of the present invention cannot delete the target DNA sequence and only gives a mutants having a mutation in the selectable marker gene (but not a deletant), the target gene is considered as essential for growth.

Modification of a gene sequence is one of the most common methods used for analyzing gene function. However, it is extremely difficult to obtain modified strains of many organisms, including *S. pombe*. In particular, when direct modification of a target gene with unknown function is unsuccessful, it cannot be clearly determined whether the failure is due to low efficiency or because the gene is essential for growth. In the method of the present invention, because the target gene is not modified during the latent stage, it is possible to produce a latent strain regardless of whether or not the target gene is essential for growth. Because through negative selection of the resulting latent strain, the strain necessarily becomes either a deletant or a mutant, either a deletant lacking the target gene is obtained or it is concluded that the region is essential for growth.

EXAMPLES

Example 1

Determination of Whether the leu1 Gene is Essential for Growth in a Leucine-Deficient Medium A DNA fragment for use in construction of deletants lacking the orotidine 5'-phophate decarboxylase gene (ura4) from the fission yeast *Schizosaccharomyces pombe* was prepared by PCR using a pair of synthetic oligoDNA primers of SEQ ID NO:1 (DNA-3620: 5'-atgtgtgcaaagaaaatcgt-3') and SEQ ID NO:2 (DNA-3621: 5'-ttacaaaatttttcaagtt-3'). The total DNA from *S. pombe* ARC032 strain (from a laboratory stock subcultured from JY1 strain obtained from Dr. Yuichi Iino at Tokyo University, Molecular Genetics Research Laboratory, genotype: h⁻) was used as the template. The amplified fragment was transformed into *S. pombe* ARC010 strain (from a laboratory stock subcultured from JY743 strain obtained from Dr. Yuichi Iino, genotype: h⁻leu1-32 ura4-D18) in accordance with Okazaki et al (Nucleic Acids Res. 18:6485-6489 (1990).) to obtain a ura4 deletant (designated as MGF300, genotype: h⁻ ura4-D18), which can grow in a minimal medium containing uracil and has recovered G at position 137 from A in the initiation codon ATG, in place of A introduced by mutation.

A DNA fragment for determination of whether the 3-isopropylmalate dehydrogenase gene (leu1) from *S. pombe* is essential for growth was prepared by using a pair of synthetic oligoDNA primers of SEQ ID NO:3 (DNA-3476: 5'-aaagag-gccaaccagaagag-3') and SEQ ID NO:4 (DNA-3477: 51-ttat-tctacattaaaccctaaaattttaatgtcaaaaaa-3') for an upstream sequence, a pair of synthetic oligoDNA primers of SEQ ID NO:5 (DNA-3478: 5'-tttcgtcaatatcacaagctcgtttac-taacgtagaaagc-3') and SEQ ID NO:6 (DNA-3479: 5'-gttgt-tgaagaagttttgtt-3') for a downstream sequence and a pair of synthetic oligoDNA primers of SEQ ID NO:7 (DNA-3482: 5'-tagggtttaatgtagaataa-3') and SEQ ID NO:6 (DNA-3483: 5'-gtgggatttgtagctaagctggatgtcgtaaatcaattcc-3') for a repeated sequence, by two-step PCR by reference to Sakurai et al. (FEMSYeast Res. 4:649-654 (2004)) and Krawchuk et al (Yeast. 15:1419-1427 (1999)) so as to contain both the ura4 sequence and a 200-bp sequence downstream of leu1 as a repeated sequence. The total DNA from ARC032 strain was used as the template for amplification. The amplified fragment was transformed into MGF300 strain by reference to Okazaki et al and Sakurai et al. (FEMSYeast Res. 4:649-654 (2004)) to obtain a strain which retained the fragment to be deleted on the chromosome and can grow on a minimal medium containing leucine and uracil (latent strain, designated as MGF375, genotype: h⁻ ura4-D18 leu1<<ura4+) (FIG. 3).

Figure 4:
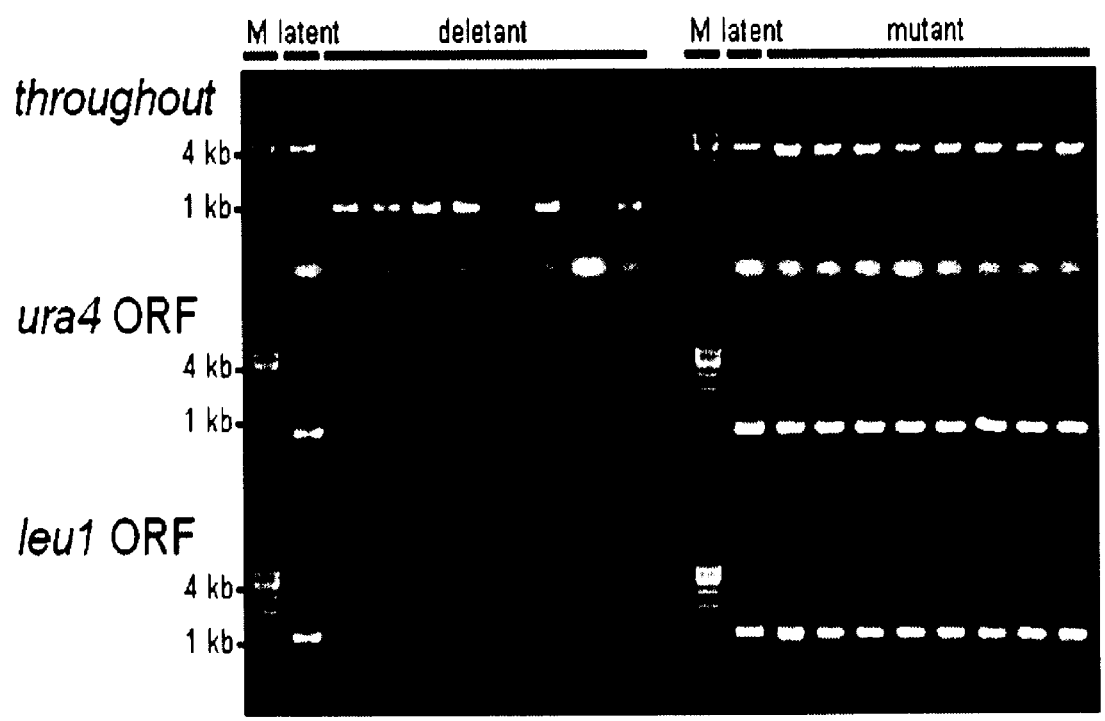
FIG. 4 Agarose gel electropherogram (stained with ethidium bromide) showing the results of identification of the target DNA region by PCR. The Left panel shows strains grown in a medium containing leucine without the need for leu1, and the right panel shows strains grown in a leucine-deficient medium with the need for leu1.

The MGF375 strain was plated on a medium containing leucine (leu), uracil (ura) and 5-fluoroorotic acid (5-FOA, indicated as FOA in the figure), and total DNA was extracted from 8 colonies among the resulting colonies. The genotypes were confirmed by PCR using a pair of synthetic oligoDNA primers of SEQ ID NO:9 (DNA-3480: 5'-aagatgacgatgat-gatttt-3') and SEQ ID NO:10 (DNA-3481: 5'-gtcgcttcttct-caacgact-3'). As a result, all the eight strains gave shorter bands than MGF375, as shown on the left-hand side of FIG. 4. PCR using a pair of synthetic oligoDNA primers of SEQ ID NO:11 (DNA-1456: 5'-atggatgctagagtatttca-3') and SEQ ID NO:12 (DNA-1457: 5'-ttaatgctgagaaagtctttg-3') designed for amplification of the ura4 sequence and PCR using a pair of synthetic oligoDNA primers DNA-3620 and DNA-3621 designed for amplification of the leu1 sequence were carried out. As a result, when both the ura4 and leu1 sequences were deleted, PCR designed for amplification throughout them gave an amplified fragment of about 1000 bp, while neither of their ORFs (ura4: 795 bp, leu1: 1116 bp) were amplified (FIG. 4, deletants). Further, in confirmation of auxotrophy, the latent strain having functional ura4 and leu1 grew on all media as shown in FIG. 5, while all the eight deletants lacking both genes were auxotrophic for uracil and leucine (FIG. 5, two out of eight deletants).

These results confirm that strains lacking not only ura4 but also the target gene leu1 (FIG. 3, deletants) were generated with high efficiency by only plating the latent strain having ura4 and a repeated sequence integrated upstream of leu1 on a medium containing 5-FOA.

Separately, the MGF375 strain was plated on a medium containing 5-FOA. Total DNA was extracted from eight out of the resulting colonies, and their genotypes were confirmed by PCR using a primer pair of DNA-3480 and DNA-3481. As a result, as shown on the right-hand side of FIG. 4, all the eight strains gave bands of the same length as MGF375 strain did. PCR using a primer pair of DNA-1456 and DNA-1457 designed for amplification of the ura4 sequence and PCR using a primer pair of DNA-3620 and DNA-3621 designed for amplification of the leu1 sequence is were carried out. As a result, when ura4 and leu1 were retained, PCR designed for amplification throughout them gave an amplified fragment of about 4000 bp, and the ORFs of ura4 and leu1 were both amplified (FIG. 4, mutants).

Figure 5:
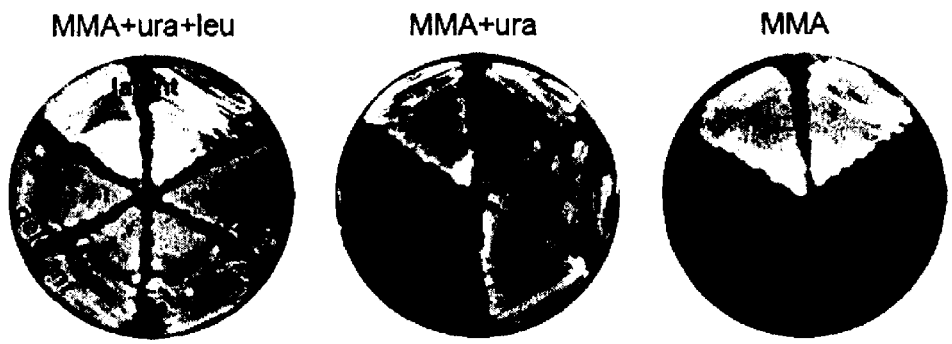
FIG. 5 Auxotrophy assay on agar media in the presence of uracil and leucine on the left-hand side, in the presence of uracil and in the absence of leucine in the middle, and in the absence of uracil and leucine on the right-hand side.

Further, in confirmation of auxotrophy, all the eight mutants which gave bands of the same length as the latent strain did were auxotrophic for uracil and prototrophic for leucine (FIG. 5, two out of eight mutants). These results confirm that strains from which neither ura4 nor leu1 have been deleted were generated with high efficiency by only plating the latent strain having ura4 and a repeated sequence integrated upstream of leu1 on a medium containing 5-FOA under culture conditions which require leu1 for growth (FIG. 4, mutant). Sequence analysis of ura4 revealed substitution of tyrosine (in two strains) or asparagines for aspartic acid at 227th position from the initiator methionine at the 1st position and substitution of lysine (in two strains) or arginine (in two strains) for threonine at the 121st position and substitution of arginine for serine at the 33rd position.

These results indicate that when the target region to be deleted contains an essential gene, the target region is efficiently deleted by homologous recombination, while when the target region contains an essential gene, mutants lacking ura4 activity due to point mutations are obtained. Namely, it is easily determined whether or not the target region contains a portion essential for growth by genotyping of the resulting strains by PCR.

Example 2

Deletion of a Long Chromosomal Region (100 kbp)

It is known that the 100-kb region (nt 5413211-5513210) near the right arm telomere of chromosome 1 in *S. pombe* contains 33 genes, none of which are known essential genes. In order to delete this region, a DNA fragment for integration of ura4 and a repeated sequence 100 kbp upstream of the gene SPAC186.06 was prepared by two-step PCR using a pair of oligoDNA primers of SEQ ID NO:13 (DNA-3350: 5'-agaat-tgagacggcgctgaa-3') and SEQ ID NO:14 (DNA-3351: 5'-gtc-cttttgttaaataaaaattaggatacactaggtagat-3') for an upstream sequence, a pair of synthetic oligoDNA primers of SEQ ID NO:15 (DNA-3352: 5'-tttcgtcaatatcacaagcttgt-tgcttttttatattaaa-3') and SEQ ID NO:16 (DNA-3353: 5'-aaa-caagactaaagattagt-3') for a downstream sequence and a pair of synthetic oligoDNA primers of SEQ ID NO:17 (DNA-3329: 5'-ttttatttaacaaaaggac-3') and SEQ ID NO:18 (DNA-3330: 5'-gtgggatttgtagctaagcttttatcgaaagaaaagaaat-3') for a repeated sequence by reference to Sakurai et al. and Krawchuk et al. as previously mentioned.

The total DNA from ARC032 strain was used as the template for amplification. The amplified fragment was transformed into ARC010 strain by reference to Okazaki et al. and Sakurai et al. as previously mentioned, to obtain a strain which retained the fragment to be deleted on the chromosome and can grow on a minimal medium containing leucine (latent strain, designated as MGF387).

Figure 6:
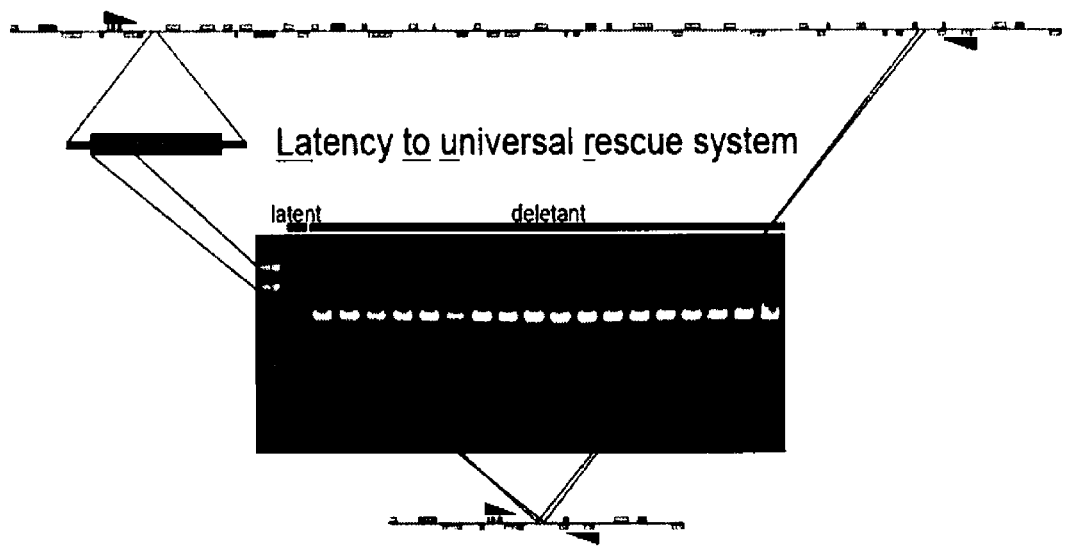
FIG. 6 Schematic representation of the gene construction near the right arm telomere of chromosome 1.
Figure 7:
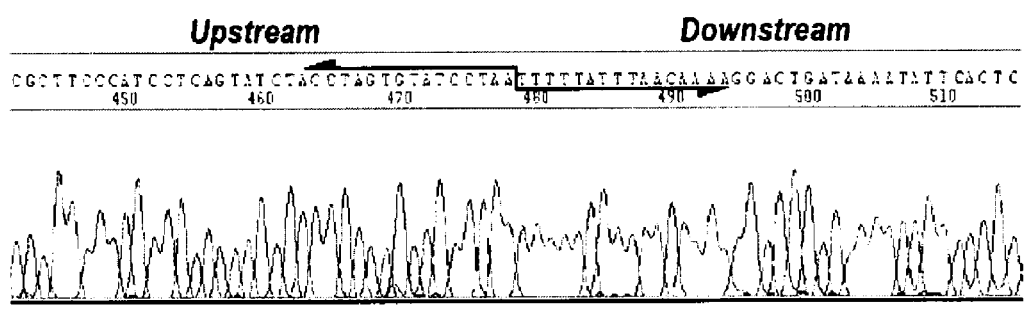
FIG. 7 Waveform image of the results of sequencing of DNA from deletants, showing seamless bonding of the regions both upstream and downstream of the deleted region.

The MGF387 strain was plated on a medium containing leucine, uracil and 5-FOA, and total DNA was extracted from 18 colonies among the resulting colonies. The genotypes were confirmed by PCR using a pair of synthetic oligoDNA primers of SEQ ID NO:19 (DNA-3354: 5'-gacagtaaaagcat-taagta-3') and SEQ ID NO:20 (DNA-3355: 5'-gctttaccaact-tcgtcaga-3'). As a result, the latent strain gave no PCR product because 100 kbp was too long to amplify, while all the eighteen 5-FOA-resistant strains gave 1000-bp bands, which indicate deletion of 100 kbp (FIG. 6). Further, DNA sequencing of the PCR products revealed that that the regions upstream and downstream of the target sequence had been connected without even a single nucleotide from the foreign sequence left between them (FIG. 7, one out of the 18 strains). The results shown in FIG. 7 confirm seamless connection of nt 5413210 and nt 5513211 on chromosome 1.

Figure 8:
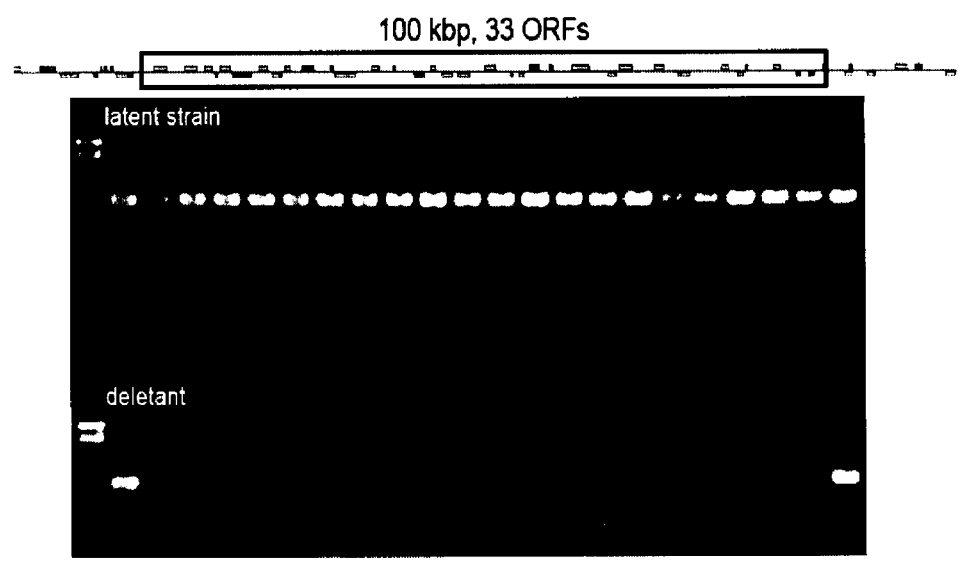
FIG. 8 Agarose gel electropherogram (stained with ethidium bromide) showing the results of ORF identification by PCR.

Further, the presence or absence of 20 out of the 33 ORFs in the 100-kbp target sequence and the ORFs adjacent to both ends of the target sequence was confirmed by primer amplification of 500-bp sequences within them. Amplification of all the ORFs was observed in the latent strain, while in the deletant treated with FOA, amplification of the ORFs was not observed except for those adjacent to both ends of the target region, which indicates deletion of 100 kbp (FIG. 8, deletant, designated as MGF388).

Industrial Applicability

The operation involved in the present invention is extremely simple and similar to the previous gene disruption method. Since its basic principle relies exclusively upon the very biological function called homologous recombination, it is likely to be able to be applied to not only various yeasts that can utilize 5-FOA, such as *S. cerevisiae* [Langle-Rouault, F. & Jacobs, E. A method for performing precise alterations in the yeast genome using a recyclable selectable marker. Nucl. Acids Res. 23, 3079-3081 (1995)], *C. albicans* [Wilson, R. B., Davis, D., Enloe, B. M. & A. P. A recyclable *Candida albicans* URA3 cassette for PCR product-directed gene disruptions. Yeast 16, 65-70 (2000)], *P. pastoris* [Nett, J. H. & Gerngross, T. U. Cloning and disruption of the PpURA5 gene and construction of a set of integration vectors for the stable genetic modification of *Pichia pastoris*. Yeast 20, 1279-1290 (2003)], *K. lactis* [Bai, X., Larsen, M. & Meinhardt, F. The URA5 gene encoding orotate-phosphoribosyltransferase of the yeast *Kluyveromyceslactis*: cloning, sequencing and use as a selectable marker. Yeast 15, 1393-1398 (1999).], but also a great variety of organisms to which negative selection is applicable such as *Escherichia coli* [Wong, Q. N. et al. Efficient and seamless DNA recombineering using a thymidylate synthase A selection system in *Escherichia coli*. Nucl. Acids Res. 33, e59 (2005)], *Arabidopsis thaliana* {Xiaohui, W. H. et al. Positive-negative selection for homologous recombination in *Arabidopsis*. Gene 272, 249-255 (2001).], mammalian cells [Mullen, C. A., Kilstrup, M. & Blaese, R. M. Transfer of the bacterial gene for cytosine deaminase to mammalian cells confers lethal sensitivity to 5-fluorocytosine: a negative selection system. Proc. Natl. Acad. Sci. USA 89, 33-37 (1992)].

The entire disclosure of Japanese Patent Application No. 2005-344749 filed on Nov. 29, 2005 including specification, claims, drawings and summary is incorporated herein by reference in its entirety.

What is claimed is:

1. A method of deleting a target DNA region from a chromosome in a yeast cell, which comprises:

integrating a DNA into the chromosome of the yeast cell, wherein the DNA comprises a sequence (A') and a negative selectable marker gene (B) connected downstream of the sequence (A'), wherein sequence (A') is substantially identical to a specific sequence (A) present downstream of the target region to cause homologous recombination between sequence (A') and sequence (A), wherein the DNA is integrated upstream of the target DNA region to form a region (X) comprising the selectable marker gene (B) and the target DNA region between sequences (A) and (A'), and then applying negative selection to the cell which causes removal of the region (X) from the chromosome by homologous recombination to obtain cells lacking the region (X).

2. The method according to claim 1, wherein the specific sequences (A) and (A') are from 50 bp to 100 bp long.

3. The method according to claim 1, wherein the target DNA region is from 500 bp to 500 kbp long.

4. The method according to claim 1, wherein the selectable marker gene (B) is an orotidine 5'-phophate decarboxylase gene.

5. The method according to claim 1, wherein the target DNA region contains a gene which complements an auxotrophy during cell growth, and homologous recombination and negative selection are carried out under culture conditions under which the gene which complements the auxotrophy is not essential.

6. A method of determining whether a target DNA region deleted from a chromosome in a yeast cell contains a gene essential for growth under desired culture conditions (Z), which comprises:

integrating a DNA into the chromosome of the yeast cell, wherein the DNA comprises a sequence (A') and a negative selectable marker gene (B) connected downstream of the sequence (A'), wherein sequence (A') is substantially identical to a specific sequence (A) present downstream of the target region to cause homologous recombination between sequence (A') and sequence (A), wherein the DNA is integrated upstream of the target DNA region to form a region (X) comprising the selectable marker gene (B) and the target DNA region between sequences (A) and (A'), carrying out homologous recombination and negative selection, wherein the homologous recombination and the negative selection are carried out under the culture conditions (Z), or the homologous recombination and the negative selection are followed by incubation of the resulting cells under the culture conditions (Z), examining yeast cells viable under the culture conditions (Z) for the presence of the target DNA region in the chromosome, and determining that the target DNA region does not contain any genes essential for growth under the culture conditions (Z), if the target DNA region is not present in the chromosome.

7. The method according to claim 6, wherein the target DNA region contains at least two genes.

8. The method according to claim 6, wherein the selectable marker gene (B) is an orotidine 5'-phosphate decarboxylase gene.

9. The method according to claim 1, wherein the yeast cell is a *S. cerevisae* cell.

10. The method according to claim 1, wherein the yeast cell is a *S. pombe* cell.

11. The method according to claim 6, wherein the yeast cell is a *S. cerevisae* cell.

12. The method according to claim 6, wherein the yeast cell is a *S. pombe* cell.

* * * * *